(12) United States Patent
Trinh et al.

(10) Patent No.: US 8,938,974 B1
(45) Date of Patent: Jan. 27, 2015

(54) METHOD FOR DETERMINING OPTIMUM INJECTOR INLET GEOMETRY

(71) Applicant: The United States of America as Represented by the Administrator of the National Aeronautics and Space Administration, Washington, DC (US)

(72) Inventors: Huu P. Trinh, Madison, AL (US); W. Neill Myers, Huntsville, AL (US)

(73) Assignee: The United States of America as represented by the United States National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 14/282,890

(22) Filed: May 20, 2014

Related U.S. Application Data (60) Division of application No. 13/452,303, filed on Apr. 20, 2012, now Pat. No. 8,763,362, which is a continuation-in-part of application No. 12/245,343, filed on Oct. 3, 2008, now abandoned.

(51) Int. Cl.
| | | |
|---|---|---|
| *F23R 3/28* | (2006.01) | |
| *F02K 9/96* | (2006.01) | |
| *G01F 1/00* | (2006.01) | |
| *G01L 7/00* | (2006.01) | |
| *G01N 33/22* | (2006.01) | |

(Continued)

(52) U.S. Cl.
CPC ... *F02K 9/96* (2013.01); *G01F 1/00* (2013.01); *G01L 7/00* (2013.01); *G01N 33/22* (2013.01); *G01L 1/005* (2013.01); *G01B 21/22* (2013.01)

USPC .................. 60/776; 60/213; 60/258; 60/741; 239/87; 239/101

(58) Field of Classification Search
USPC ........ 60/39.23, 213, 233, 257, 258, 737, 738, 60/739, 740, 741, 742, 746, 747, 259, 60/776; 239/86, 87, 88, 89, 90, 91, 92, 239/101; 137/512.1; 29/407.01, 407.05
See application file for complete search history.

(56) References Cited

U.S. PATENT DOCUMENTS

| | | | | |
|---|---|---|---|---|
| 3,391,533 A | * | 7/1968 | Mageean | 60/39.27 |
| 3,464,633 A | * | 9/1969 | Potocnik | 239/425 |
| 3,468,487 A | * | 9/1969 | Warren | 239/403 |

(Continued)

OTHER PUBLICATIONS

Doumas, M., Laster, R.; Liquid-Film Properties for Centrifugal Spray Nozzles; Chemical Engineering Progress; Oct. 1953; pp. 518-526; vol. 49, No. 10; General Foods Corporation; Hoboken, NJ, USA.

*Primary Examiner* — Gerald L Sung
*Assistant Examiner* — Michael B Mantyla
(74) *Attorney, Agent, or Firm* — Absolute Technology Law Group, LLC; James J. McGroary (57) ABSTRACT

A method for determining the optimum inlet geometry of a liquid rocket engine swirl injector includes obtaining a throttleable level phase value, volume flow rate, chamber pressure, liquid propellant density, inlet injector pressure, desired target spray angle and desired target optimum delta pressure value between an inlet and a chamber for a plurality of engine stages. The method calculates the tangential inlet area for each throttleable stage. The method also uses correlation between the tangential inlet areas and delta pressure values to calculate the spring displacement and variable inlet geometry of a liquid rocket engine swirl injector.

6 Claims, 9 Drawing Sheets

(51) Int. Cl.
  *G01L 1/00*     (2006.01)
  *G01B 21/22*    (2006.01)

(56) References Cited

U.S. PATENT DOCUMENTS

| | | | | |
|---|---|---|---|---|
| 3,474,621 | A | * | 10/1969 | Zimmet .................. 60/39.48 |
| 3,476,134 | A | * | 11/1969 | Kemp .................. 137/115.13 |
| 3,482,397 | A | * | 12/1969 | Luperi et al. .................. 60/740 |
| 3,515,353 | A | * | 6/1970 | Potocnik et al. ............. 239/414 |
| 3,544,061 | A | * | 12/1970 | Huniu et al. .................... 251/24 |
| 3,726,088 | A | * | 4/1973 | Kretschmer et al. ............ 60/741 |
| 3,780,952 | A | * | 12/1973 | Huang ........................ 239/424.5 |
| 4,350,009 | A | * | 9/1982 | Holzapfel .................... 60/39.23 |
| 4,360,161 | A | * | 11/1982 | Claxton et al. ................ 239/463 |
| 4,427,151 | A | * | 1/1984 | Trenne ............................ 239/87 |
| 4,621,492 | A | * | 11/1986 | von Pragenau ................. 60/258 |
| 4,629,127 | A | * | 12/1986 | Kawamura et al. ............ 239/489 |
| 4,782,660 | A | * | 11/1988 | Domyan et al. ................ 60/258 |
| 5,137,046 | A | * | 8/1992 | Sollman et al. ............. 137/115.1 |
| 5,660,039 | A | * | 8/1997 | Sion et al. ....................... 60/258 |
| 5,873,998 | A |   | 2/1999 | Grangeon et al. |
| 6,116,020 | A | * | 9/2000 | Cornelius et al. .............. 60/258 |
| 6,227,175 | B1 | * | 5/2001 | Jiang et al. ................... 123/496 |
| 6,253,539 | B1 | * | 7/2001 | Farhangi et al. ................ 60/211 |
| 6,405,947 | B2 | * | 6/2002 | Fochtman .................. 239/585.4 |
| 6,484,700 | B1 | * | 11/2002 | Kimmel et al. ............... 123/531 |
| 6,895,755 | B2 | * | 5/2005 | Steinthorsson et al. ........ 60/742 |
| 7,048,253 | B2 | * | 5/2006 | Stier ........................ 251/129.21 |
| 7,114,518 | B2 | * | 10/2006 | Kirby ............................ 137/504 |
| 7,640,726 | B2 | * | 1/2010 | Fang et al. ...................... 60/204 |
| 7,703,274 | B2 | * | 4/2010 | Hasegawa et al. ............. 60/258 |
| 2002/0063479 | A1 | * | 5/2002 | Mitchell et al. ................ 307/153 |
| 2002/0124549 | A1 | * | 9/2002 | Dittmann et al. ............ 60/39.23 |
| 2006/0230745 | A1 | * | 10/2006 | Hasegawa et al. ............. 60/258 |
| 2006/0254278 | A1 | * | 11/2006 | Schoell ........................... 60/670 |
| 2009/0320447 | A1 | * | 12/2009 | Fisher ............................. 60/258 |
| 2010/0043392 | A1 | * | 2/2010 | Jung ............................... 60/222 |

* cited by examiner

METHOD FOR DETERMINING OPTIMUM INJECTOR INLET GEOMETRY

CROSS-REFERENCES TO RELATED APPLICATIONS

This application is a divisional application of U.S. patent application Ser. No. 13/452,303, filed on Apr. 20, 2012, which is a continuation-in-part application of U.S. patent application Ser. No. 12/245,343, filed on Oct. 3, 2008, which are hereby incorporated by reference in their entirety.

FEDERAL RESEARCH STATEMENT

The invention described herein was made by employees of the United States Government and may be manufactured and used by or for the Government of the United States of America for governmental purposes without the payment of any royalties thereon or therefore.

FIELD OF INVENTION

This invention relates to propellant injection elements, and more specifically to a method for determining the optimum inlet geometry of a liquid rocket engine swirl injector.

TERMINOLOGY

As used herein, the term "chamber pressure" refers to the pressure in a combustion chamber, as measured in pounds per square inch. In some instances, hot gasses created by the burning of fuel or propellants may cause chamber pressure. Propellants are composed of fuel and oxidizer.

As used herein, the terms "discharge coefficient" or "K" refer to the fluid resistance as fluid flows from an injector inlet to a combustion chamber. K may be calculated using the equation:

$$K = \frac{\alpha(1-\alpha)^{1/2}}{(1-\alpha+\alpha^2 A^2)^{1/2}}$$

where $$\alpha = 1 - \frac{r_{ac}^2}{r_h},$$

$$A = \frac{\pi r_h R}{a},$$

$r_{ac}$ is the radius of the gas core inside an injector post, $r_h$ is the radius of the outlet of an injector post, and R is the radius of an injector post as measured adjacent to the outlet.

As used herein, the term "geometric effectiveness coefficient" refers to the difference in flow resistance between a circular passage and a non-circular passage for equal area, represented by the term $d_{eff}$. For a circular passage, $d_{eff}$ is equal to 1. As passages deviate from circular, $d_{eff} < 1$.

As used herein, the term "inlet pressure" refers to the pressure in the inlet manifold of an engine.

As used herein, the term "optimum delta pressure value" refers to the minimum pressure difference between the pressure of an injector inlet and the pressure of a combustion chamber.

As used herein, the term "spray angle" refers to the cone angle of the spray pattern measured relative to the injector outlet. In some instances, a half spray angle, or the angle of a spray measured relative to a centerline perpendicular with an outlet, may be used in place of a full spray angle.

As used herein, the term "target throttleable range" or "TTR" refers to the preferred range of adjustable thrust level at which an engine is desired to operate.

As used herein, the term "throttleable level phase value" or "TLPV" refers to a specific throttling level, or power level, within a target throttleable range.

As used herein, the term "volume flow rate" or "V" refers to the rate of propellant in volume entering an engine as measured in cubic feet per second.

BACKGROUND OF THE INVENTION

The speed of a rocket depends on thrust and the rocket's weight. Thrust is a measure of the force generated from propellant combustion ejected from the rear of the rocket and speed at which the propellant is used. Increased thrust, relative to the rocket's weight, results in greater speed.

Specific impulse is the change in momentum per unit mass for rocket fuels. Specific impulse is a measurement of how much push accumulates as the rocket consumes fuel, or, in terms of thrust, is a rough measurement of how fast the rocket ejects propellant. A rocket having a high specific impulse does not require as much fuel because the rocket gets more push per amount of fuel.

Some rocket engines are variable thrust engines. Variable thrust engines do not have a constant thrust. Rockets having a variable thrust engine, therefore, can generate levels of thrust as needed on demand throughout its flight mission. Hence, the rocket has better control and performance than one with constant thrust engines.

While variable thrust engines are capable of generating levels of thrust as needed on demand for a mission or solar system exploration, it is difficult to control the variable amount of fuel required for the desired thrust.

Throttling an engine increases or decreases the amount of thrust. Throttling adjusts the power level of an engine within its target throttleable range, resulting in an adjustment of the amount and mixture of fuel and oxidizer reaching the engine. However, it is very difficult to control the proper mixing and amount of fuel and oxidizer at low power levels. As a result, engines do not have optimum performance for an entire throttleable range and tend to chug which leads to engine and rocket damage. Most variable thrust engines for rockets are therefore designed to operate only within a small target throttleable range.

It is desirable to design fuel injection systems which can achieve the broadest possible target throttleable range and, in particular, which can offer control of an engine at low thrust levels while maintaining an optimum performance. High performance for a wide range of thrust levels is achieved by controlling the injector inlet area while maintaining adequate pressure drop and good mixing of fuel and oxidizer.

Various attempts have been made in the prior art to control the rate of mixing and the structure of the fuel and oxidizer streams that are created when injecting fuel and oxidizer into the combustion chamber. Throttling is the process of adjusting the position of elements within an engine to release propellant into its combustion chamber. Traditionally the throttling of a liquid fuel engine occurs through valves, which adjust the fuel and oxidizer flow. Control of a mixing process is particularly critical to engines.

For example, U.S. Pat. No. 3,726,088 discloses an injection element that varies the rate of fuel into the fuel manifold by increasing and decreasing the area of the inlet slot. However, the variable inlet slot is only one physical means of controlling a mixing interface. Injection elements have many components and geometric characteristics that can theoretically be altered to vary the structure of the fuel and oxidant streams to increase the level of control over the mixing interface.

There is an unmet need in the prior art for a method for determining specific injection area geometries to accommodate specific applications, engines and throttling requirements.

SUMMARY OF THE INVENTION

The present invention is a method for determining the optimum inlet geometry of a liquid rocket engine swirl injector and resulting injector. It is possible to calculate the tangential inlet area for each throttleable level phase value by obtaining values specific for a given engine and application. These values include a throttleable level phase value, volume flow rate, chamber pressure, liquid propellant density, inlet injector pressure, desired target spray angle between 60 and 90 degrees and desired target optimum delta pressure value between an inlet and a chamber for a plurality of engine stages. A user then utilizes correlation between these tangential inlet areas and the delta pressure values to calculate the spring displacement and the variable inlet geometry of a liquid rocket engine swirl injector.

DETAILED DESCRIPTION

For the purpose of promoting an understanding of the present invention, references are made in the text to exemplary embodiments of an injector element that maintains a constant mean spray angle and optimum pressure drop during throttling by varying the geometry of tangential inlets, only some of which are described herein. It should be understood that no limitations on the scope of the invention are intended by describing these exemplary embodiments. One of ordinary skill in the art will readily appreciate that alternate but functionally equivalent materials, components, and steps may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

Figure 1:
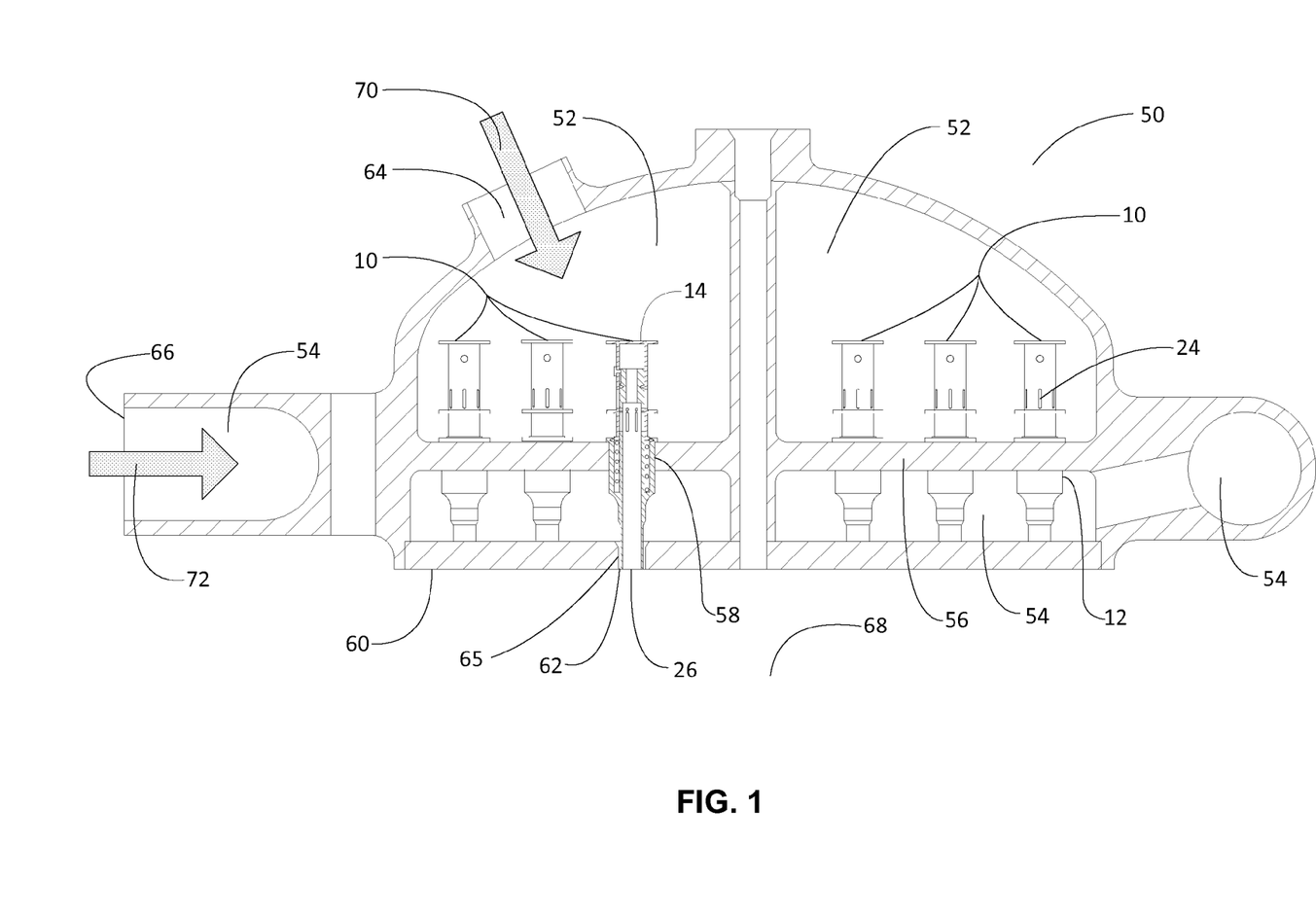
FIG. 1 is an exemplary embodiment of an injector with multiple injector elements.
Figure 2A:
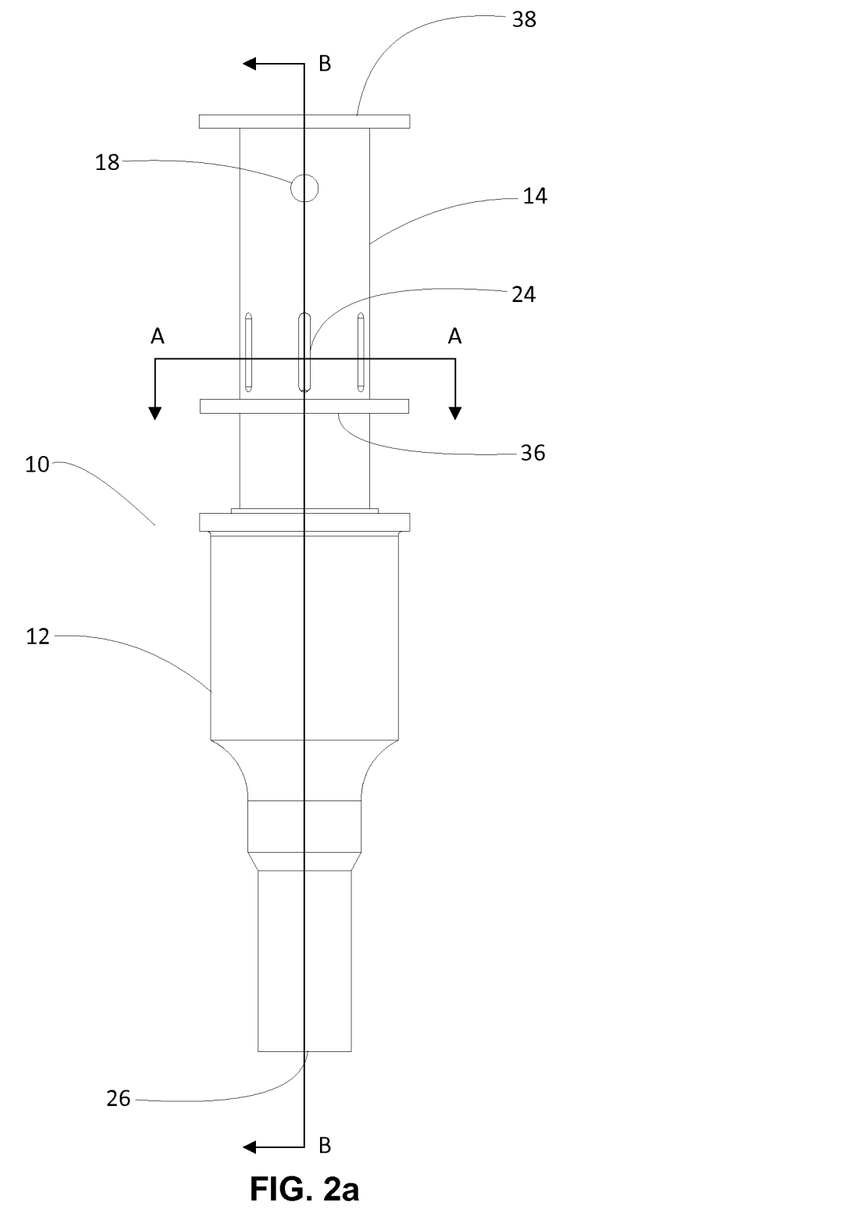
FIGS. 2a and 2b illustrate an exemplary embodiment of an injector element.
Figure 2B:
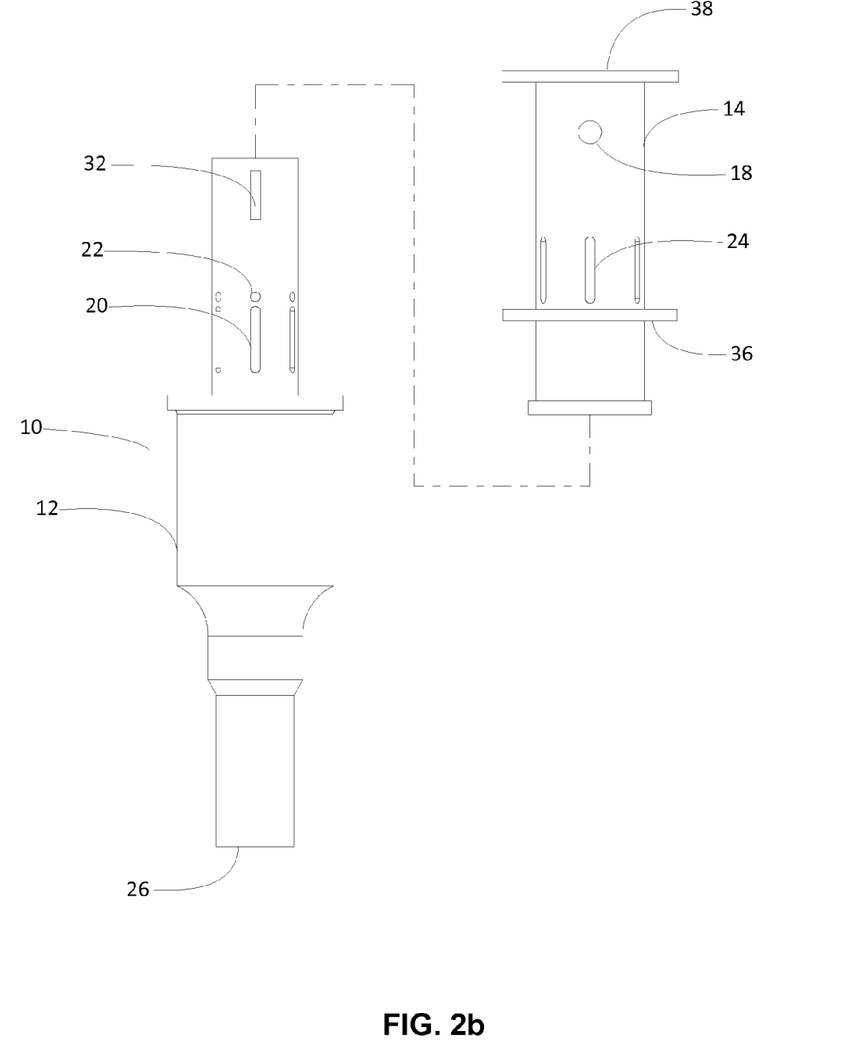

FIG. 1 is an exemplary embodiment of combustion chamber injector 50 with multiple injector elements 10, which will be shown in further detail in FIG. 2.

In the exemplary embodiment shown, injector 50 has oxidizer manifold 52 for receiving an oxidizer, fuel manifold 54 for receiving a fuel, a multiplicity of injector elements 10, and faceplate 60, which separates injector 50 from combustion chamber 68. As illustrated, injector elements 10 are installed and arranged within injector 50 in a concentric array, but in further exemplary embodiments, injector elements 10 may be arranged in any desired pattern or arrangement.

Oxidizer manifold 52 and fuel manifold 54 are separated by inter-propellant plate 56 into which injector elements 10 are brazed at braze joints 58. In further exemplary embodiments, injector elements 10 may be secured within inter-propellant plate 56 by any means known in the art. Injector elements 10 protrude through openings 65 in faceplate 60 with element outlets 26 flush with the lower surface of the faceplate 60. Openings 65 of faceplate 60 are larger in diameter than element outlets 26, providing annular passage 62 for the fuel to flow through the faceplate 60.

As illustrated in FIG. 1, injector 50 injects propellants into combustion chamber 68. Oxidizer 70 enters manifold 52 through port 64 and surrounds injector elements 10. Initially, oxidizer 70 will flow through slots 24 in injection tube cap 14 and then through small tangential holes 22 (not shown), as will be later described.

Tangential inlet holes 22 (not shown) cause oxidizer 70 to swirl as it progresses down injection tube 12 and exits into combustion chamber 68 at outlet 26. Fuel 72 enters fuel manifold 54 through port 66 and proceeds towards the injector elements 10, where fuel 72 flows through annular passages 62, which surround each injection tube 12, and exits through faceplate 60 to enter combustion chamber 68.

The swirling oxidizer streams and the annular fuel streams mix and combust to generate power. As an engine's power level increases, the pressure variation between oxidizer manifold 52 and the interior of the injector element 10 becomes larger. This results in a stronger force pushing injection cap 14.

In the exemplary embodiment shown, injector elements 10 are identical. However, in further exemplary embodiments, injector elements 10 may not be identical, and variations in injector element 10 design may be based on specific design considerations. These design considerations include, but are not limited to, the target throttleable range of a specific engine, the volume flow rate, the chamber pressures, the density of the propellant, the viscosity of the propellant, the injector inlet pressure, the desired target spray angle and the desired target optimum delta pressure value between the inlet and the chamber.

FIGS. 2a and 2b illustrate an exemplary embodiment of injector element 10 with inlet slots 24. Injector element 10 includes injection tube 12 covered with injection tube cap 14. Injection tube cap 14 slides axially up and down injection tube 12.

Injection tube 12 also includes tangential inlets 20 and small tangential inlet holes 22. Tangential inlets 20 and small tangential inlet holes 22 are cut so that they are tangential to the inner wall of injection tube 12.

Pins 18 protrude into grooves within injection tube's 12 outer wall and allow injection tube cap 14 to translate axially. Pins 18 also keep inlet slots 24 in injection tube cap 14 aligned with tangential slots 20 in injection tub 12. The exemplary embodiment described uses two pins 18. In further exemplary embodiments, any number of pins 18 may be used. In still further exemplary embodiments, any structure or device known in the art to prevent injection tube cap 14 from disengaging injection tube 12 while still providing movement may be used.

Injector element 10 also includes flanges 36 and 38, which extend into surrounding fluid and damp any resonant motion that may develop.

Figure 3:
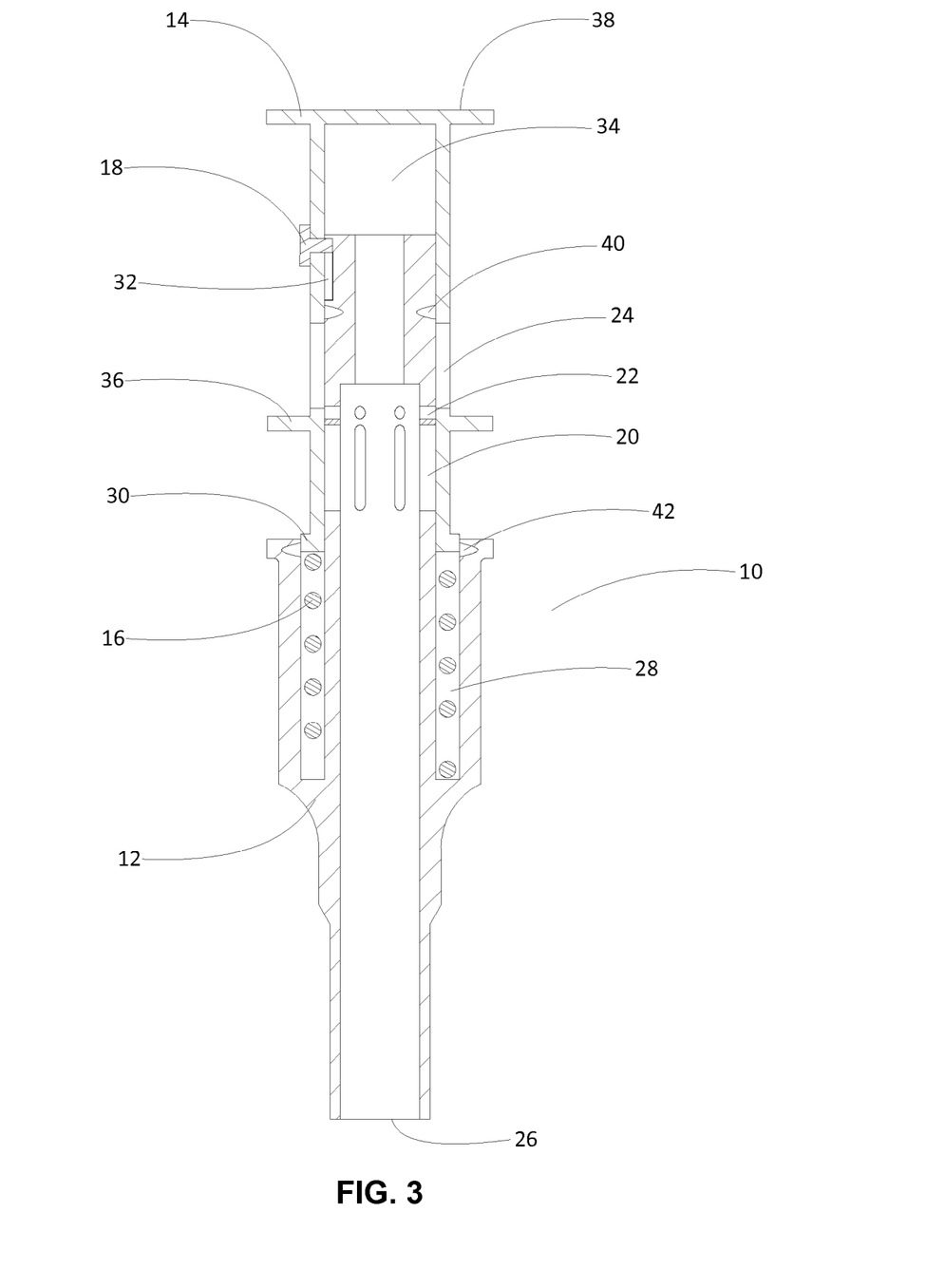
FIG. 3 is a cross sectional view of an exemplary injector element.

FIG. 3 is a cross sectional view of an exemplary injector element 10 taken along B-B. As illustrated, injection tube cap 14 with inlet slots 24 slides axially up and down injection tube 12. Pins 18 slidably secure injection tube 14 to injection tube 12 at grooves 32, which are elongated to allow injection tube cap 14 to move axially for its full range of motion. Pins 18 also prohibit rotational movement and keep inlet slots 24 in injection tube cap 14 aligned with tangential inlets 20 and small tangential inlet holes 22 in injection tube 12.

Also illustrated in FIG. 3 is spring mechanism 16, which in the exemplary embodiment shown is a coil spring. Spring mechanism 16 is assembled within spring recess 28. Spring mechanism 16 is compressed with one end seated in the bottom of spring recess 28 and the other end pressing upward on end flange 30 of injection tube cap 14. Labyrinth type seals 40 and 42, between the top of injection tube 12 and injection tube cap 14 and where injection tube cap 14 meets spring mechanism 16, respectively, prevent leakage so that oxidizer flow must enter injection tube 12 through either tangential inlets 20 or small tangential holes 22.

In the exemplary embodiments described, above, injector element 10 is designed so that at rest, with no pressure difference between injection tube cap 14 and element outlet 26, spring mechanism 16 keeps injection tube cap 14 pushed upward so that inlet slots 24 are not axially aligned with small tangential inlet holes 22 or tangential inlets 20. Oxidizer is therefore unable to enter injection tube 12.

Changes in pressure move injection tube cap 14 towards recess 28 and cause spring mechanism 16 to compress. Spring mechanism 16, however, will oppose this movement by pushing on injection tube cap 14 in a direction away from spring recess 28. This opposing force of spring mechanism 16 is the result of the force constant (K), or stiffness.

At low engine power levels, such as when the engine is throttled back, the opposing force of spring mechanism 16 is closer to the force supplied by the pressure change, and injection tube cap 14 therefore moves only slightly towards spring recess 28. Small tangential inlet holes 22 are then aligned with inlet slots 24, allowing a small amount of flow though injector element 10. In the exemplary embodiment shown, small tangential inlet holes 22 are designed to be fully open at low engine power levels. In further exemplary embodiments, small tangential inlet holes 22 may have a different design or configuration so that only a portion of the area of small tangential inlet holes 22, or only some of small tangential inlet holes 22, are open.

In some exemplary embodiments, this initial injection inlet area ($A_{inj}$) may be specifically calculated to correspond to the lowest desirable engine power level.

As the engine power increases, the pressure variation between oxidizer manifold 52 (not shown) and the interior of the injector element 10, denoted as $\Delta P$, rises and becomes increasingly greater than the stiffness (k) of spring mechanism 16. Injection tube cap 14 therefore pushes further downward along injection tube 12, so that tangential inlets 20 align with inlet slots 24, allowing increased flow as pressure increases.

As $\Delta P$ rises, the force acting on spring mechanism 16 is determined by $\Delta PA_{cap}$, where $A_{cap}$ is the area of the injection tube cap 14. Subsequently, spring mechanism 16 is compressed by the subject force and the injection tube cap 14 translates downward a distance of $\Delta X$ referenced to the initial preloaded position:

$$\Delta X = \frac{\Delta PA_{cap} - F}{k}$$

It should be noted that the cap moves as long as $\Delta PA_{cap} \geq F$, where F is the preloaded compression force of spring mechanism 16. As noted above, the desirable inlet area for a certain engine power level can be estimated by injector designers for optimum performance.

Considering that the injection tube cap 14 will slide a distance of $\Delta X$, the geometry of the tangential inlets 20 can be designed in such a way that the opening area of the inlets 20 is equal to the desirable inlet area. As injection tube cap 14 moves downward, inlet slot 24 of injection tube cap 14 and tangential inlets 20 of injection tube 12 start to overlap until they are coincident with each other. This overlap is proportional to the additional oxidizer allowed to flow through each injection element 10 on its way to combustion chamber 68 (not shown).

Figure 6:
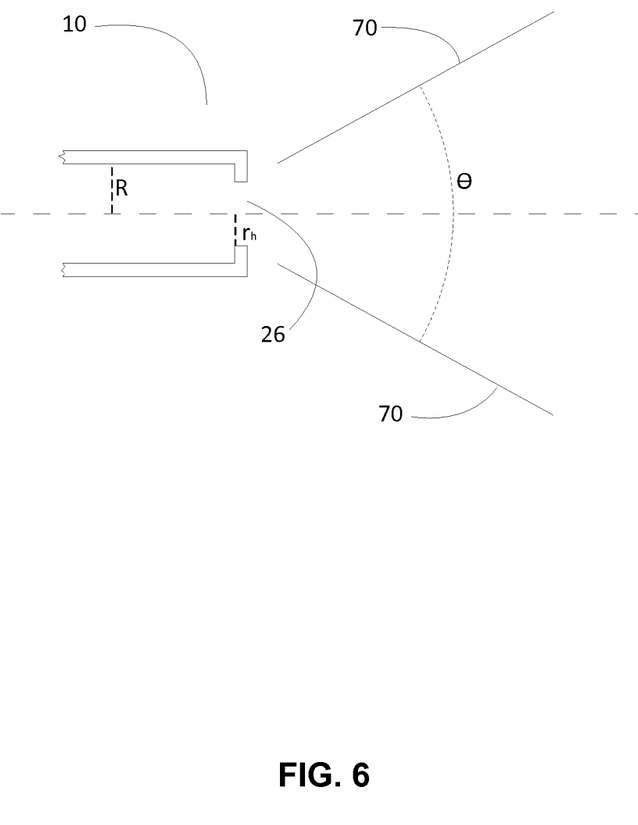
FIG. 6 illustrates flow out of an exemplary injector element.

As an engine is throttled back, the propellant volume flow rate ($\dot{V}$) needs to be reduced. The pressure drop across injector element 10 will reduce more drastically than the volume flow rate when an engine is throttled back, and this pressure drop must be controlled to maintain engine stability and optimum propellant mixing. Ideally, the ratio of the pressure drop across injector element 10 ($\Delta P$) and the pressure in the combustion chamber ($P_c$), or $\Delta P/P_c$, should remain above 15%, while the spray angle $\theta$, as illustrated in FIG. 6, has a mean value between 60 and 90 degrees. Maintaining these values will provide a good mixing between fuel and oxidizer for high combustion performance.

To avoid a drastic drop in $\Delta P$ when throttling back, the injector discharge coefficient (K) should be reduced to compensate for the drop in $\Delta P$. The injector discharge coefficient is determined using the equation:

$$K = \frac{\alpha(1-\alpha)^{1/2}}{(1-\alpha+\alpha^2 A^2)^{1/2}}$$

where $$\alpha = 1 - \frac{r_{ac}^2}{r_h},$$

$$A = \frac{\pi r_h R}{a},$$

$r_{ac}$ is the radius of the gas core inside an injector post, $r_h$ is the radius of the outlet of an injector post, and R is the radius of an injector post as measured adjacent to the outlet.

These equations show that K may be reduced by making the tangential inlet area (a) physically smaller when the engine is throttling down. However, making a too small would reduce the spray angle, so it is necessary to balance changes in K with changes in the spray angle to maintain a mean spray angle between 60 and 90 degrees.

Figure 4:
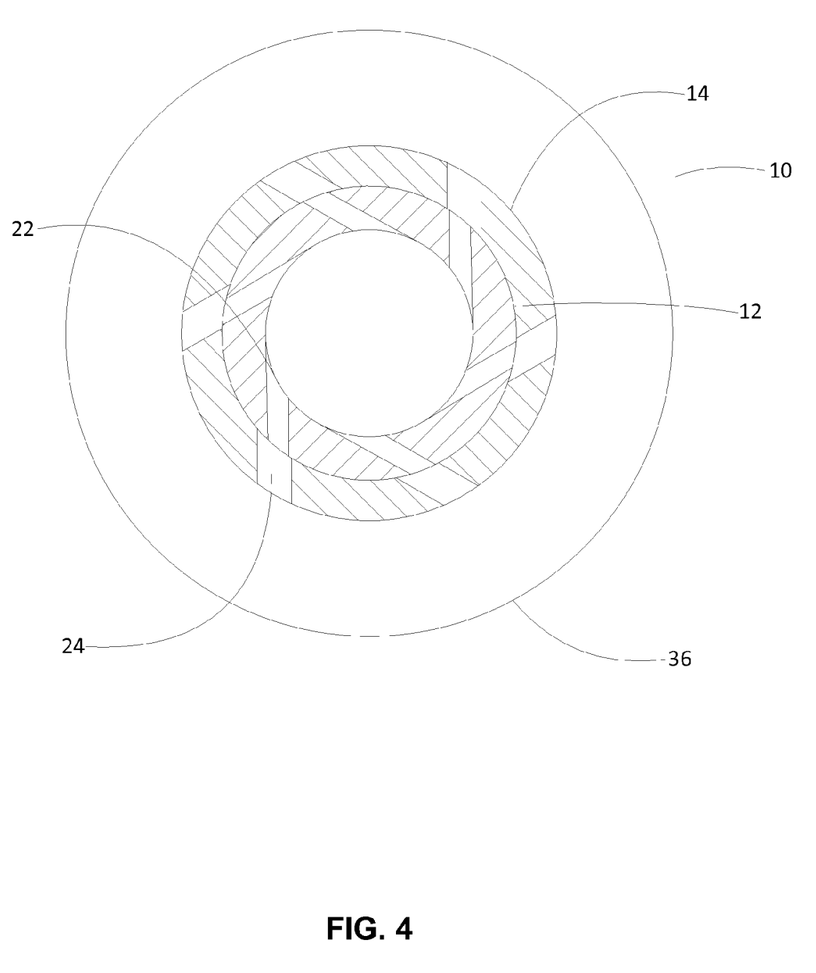
FIG. 4 is a top section view of an exemplary injector element.

FIG. 4 is a top section view of an exemplary injector element 10 taken along A-A, showing inlet slots 24 of injection tube cap 14 aligned with small tangential inlet holes 22 of injection tube 12. Initially, oxidizer will flow through inlet slots 24 in injection tube cap 14 and then through small tangential inlet holes 22. These small tangential inlet holes 22 cause the oxidizer to swirl as it progresses down injection tube 12 and exits at element outlet 26 into combustion chamber 68 (not shown).

Specifically, in the exemplary embodiment shown, it is the angled design of inlet slots 24 and small tangential inlet holes 22, as measured relative to a line drawn perpendicular to and through the center of injector element 10, which creates the swirling stream of oxidizer. If inlet slots 24 and small tangential inlet holes 22 are more perpendicular to that central reference line, oxidizer will not swirl or swirl as successfully.

Similarly, tangential inlets 20 (not shown), angled relative to a line drawn perpendicular to and through the center of injector element 10, create a swirling motion as oxidizer or other fluid enters injection tube 12.

The tangential angle of tangential inlets 20 (not shown) and tangential inlet holes 22, as well as the tangential angle of inlet slots 24, causes oxidizer to swirl as it enters injection tube 12, resulting in the oxidizer exiting injection tube 12 at an angle between 60 and 90 degrees.

As illustrated in the exemplary embodiments shown in FIGS. 1 through 4, inlet slots 24 of injection tube cap 14 and tangential inlets 20 of injection tube 12 are rounded rectangular slots. However, in further exemplary embodiments, the specific shapes of inlet slots 24 and tangential inlets 20 may vary.

Figure 5:
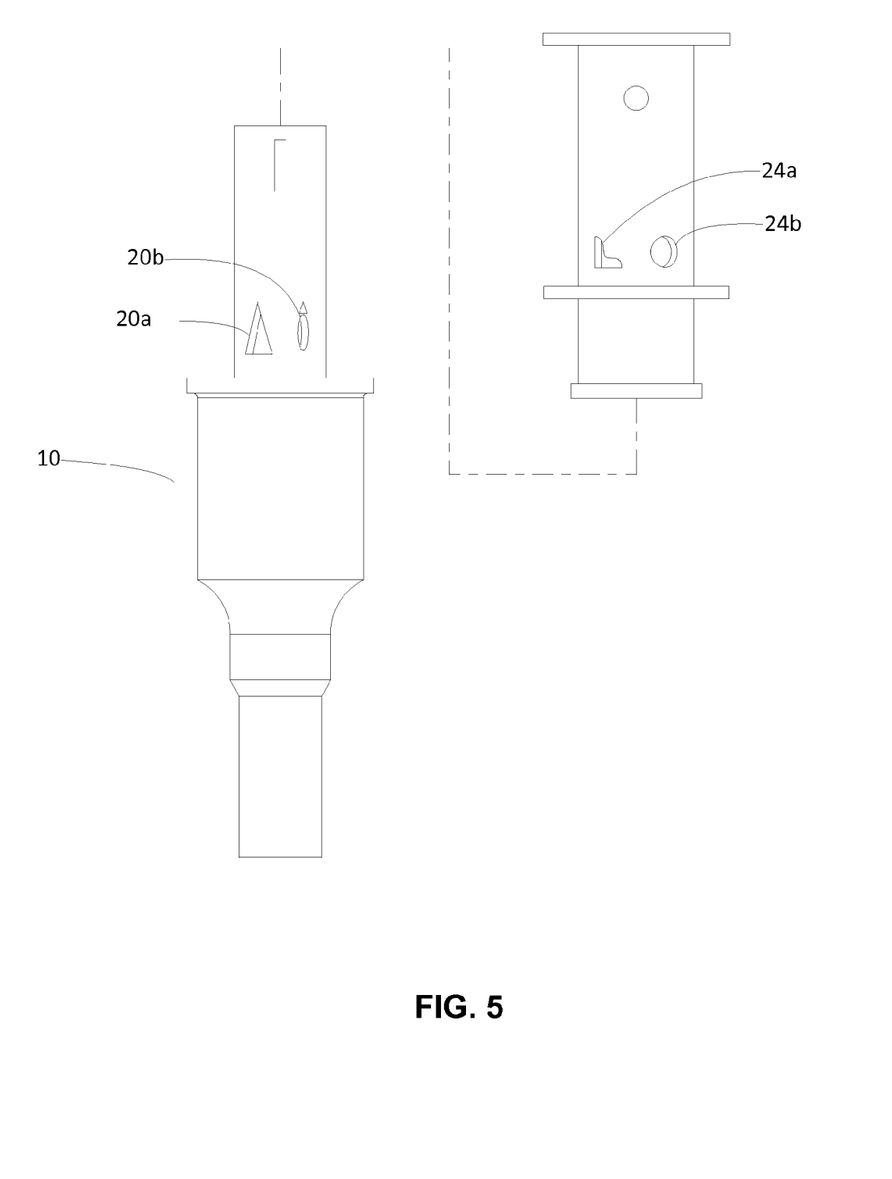
FIG. 5 is an illustration of an alternative injector element with geometrically varying inlets.

In the exemplary embodiment shown in FIG. 5, injector element 10 displays a variety of inlet slot 24 and tangential inlet 20 geometries. For example, inlet slot 24a is an irregular polygon, while inlet slot 24b is circular. Similarly, tangential inlet 20a is long and angular, while tangential inlet 20b is made of two separate apertures, with the first being triangular and the second being oval. By providing different geometries for inlet slots 24 and tangential inlets 20, the amount of flow through the slots may be specifically controlled at each pressure difference.

While this specific configuration of inlet slots 24 and tangential inlets 20 may not be specifically used together as a practical matter because some areas of inlet slots 24 and tangential inlets 20 will never overlap, the exemplary embodiment depicted in FIG. 5 illustrates exemplary alternate geometries for inlets slots 24 and tangential inlets 20.

In further exemplary embodiments, inlet slots 24 and tangential inlets 20 may have any shape, size or geometry that allows for a variable flow rate through injector element 10. In still further exemplary embodiments, the specific geometry for inlet slots 24 and tangential inlets 20 may be specifically calculated for a given engine type, throttle range and desired flow rate.

For an optimum injector element 10 design, the preferred injection pressure drop $\Delta P$ and inlet area would change with the engine power level. In general, the higher the power level is, the higher the pressure drop and the larger the inlet area. Furthermore, the relationship between the pressure drop and the inlet area may be different among the different injector types. For a swirling injection element, formulations of the pressure drop and the inlet area developed by Doumas and Laster are widely used. Doumas, M., Laster. R. "Liquid-Film Properties for Centrifugal Spray Nozzles," Chemical Engineering Progress, Vol. 49: No. 10. October 1953, p. 518-526.

FIG. 6 is an exemplary embodiment of injector element 10 with oxidizer 70 swirling from element outlet 26. As illustrated, oxidizer 70 exits injector element 10 in a conical swirl having an angle $\theta$ between 60 and 90 degrees. This spray angle range is critical to properly mix oxidizer 70 and propellant 72 (not shown), which flows through annular passage 62. In some exemplary embodiments, a half spray angle $\theta_{1/2}$ is measured by determining the angle of the spray from a centerline perpendicular to element outlet 26.

While the exemplary embodiments above describe injection elements 10 for use with rocket engines, injection elements 10 as described herein may be used with any combustors, diesel engines, gas turbine engines, medical applications and any spray applications, including, but not limited to, spray applications in the food and painting industries. Injector element 10 may be used in any injection type application as long as the inlets may be used to control the injection pressure drop.

Figure 7:
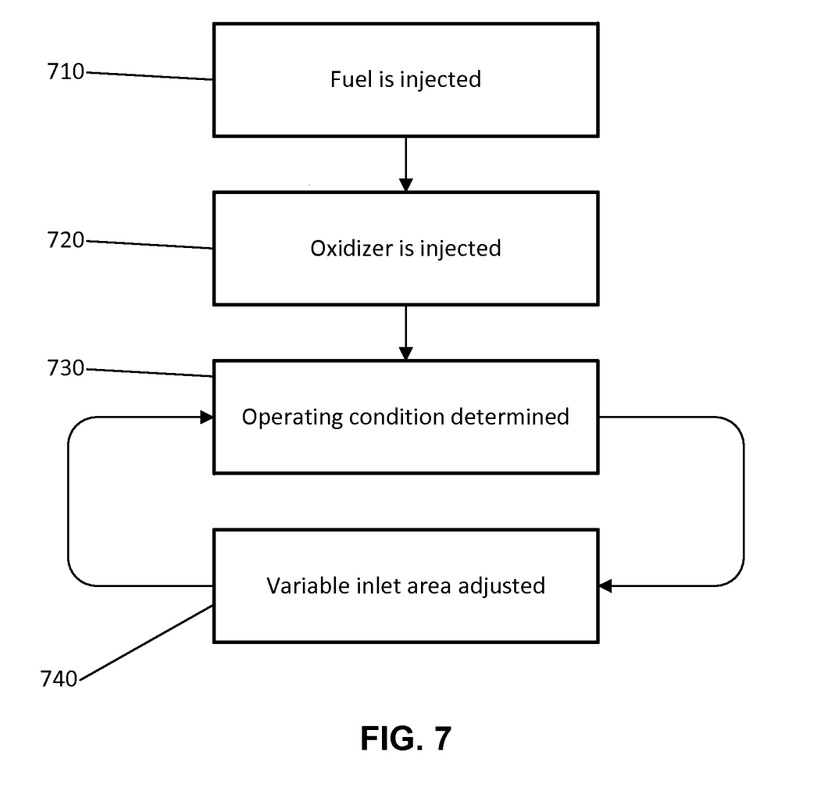
FIG. 7 is a flowchart of a method to control propellant injection into a combustion chamber in accordance with an embodiment.

FIG. 7 is a flowchart of method to control propellant injection into a combustion chamber 700. First, in Step 710, fuel is injected, followed by oxidizer in Step 720. An operating condition, such as pressure, is determined (Step 730), and the variable inlet area is adjusted based on the operating condition (Step 740). Steps 730 and 740 are then continually repeated, forming a feedback loop, so that as the operating condition (i.e., pressure) changes and is re-determined (Step 730), the variable inlet area is continually adjusted in response (Step 740).

Method 700 is performed by the combination of the multiplicity of injection elements 10 (not shown), oxidizer and fuel processed through injector 50 (not shown). The variable inlet area is adjusted (Step 740) by the interaction of injection tube cap 14 (not shown), spring mechanism 16 (not shown), and the change in pressure. The change in variable inlet area is correlated to pressure variations at the injection tube cap 14 (not shown). The net result of the interaction is to regulate the amount of oxidizer entering the combustion chamber by adjusting the variable inlet area of each injector element based on a change in pressure.

The additional flow passing through tangential inlet holes 22 (not shown) will increase the pressure drop creating a larger delta pressure between manifold 52 (not shown) and the interior of injection tube 12 (not shown) and injection tube cap 14 (not shown). The delta pressure between manifold 52 (not shown) and cap interior 34 (not shown) creates a force, which compresses spring mechanism 16 (not shown) when injection tube cap 14 (not shown) translates downward. The translation of injection tube cap 14 (not shown) allows inlet slots 24 (not shown) to partially expose tangential inlets 20 (not shown) in injection tube 12 (not shown), increasing the flow area into the tube.

Due to the tangential nature of tangential inlets 20 (not shown), the additional flow will also swirl as it progresses down injection tube 12 (not shown). Thus, the pressure drop and resulting pressure ratio between the injector inlet and combustion chamber 68 (not shown) will adjust to maintain the optimum value for high performance at the higher power level. The number and size of tangential inlets 20 (not shown) in conjunction with the stiffness (k) of spring mechanism 16 (not shown) are selected to produce the optimum pressure ratio for a given power level.

As the engine power level increases, injection elements 10 (not shown) will continue to adjust to maintain an optimum pressure ratio until tangential inlets 20 (not shown) reach full exposure at 100% power level (i.e., tangential inlets 20 (not shown) and inlet slots 24 (not shown) coincide with each other.)

Labyrinth seal grooves 40, 42 (not shown) limit leakage whether or not the tangential inlets 20 and tangential slots 24 are aligned with each other. Labyrinth seal grooves 40, 42 (not shown) prevent oxidizer from entering injection tube 12 (not shown) by bypassing tangential inlets 20 (not shown). As injection tube cap 14 (not shown) moves or pushes against spring mechanism 16 (not shown) to adjust the pressure ratio, flanges 36 and 38 (not shown), which extend into the surrounding fluid, damp any resonant motion which may tend to develop.

Method 700 combines spring mechanism 16 (not shown), injection tube cap 14 (not shown), and strategically positioned tangential inlets 20 (not shown) to act as a mechanism in each injector element 10 (not shown) to automatically adjust the variable inlet area based on an operating condition so as to maintain optimum performance throughout the wide throttling range of the engine.

In the exemplary embodiment described, method 700 utilizes the differential pressure between the injection element inlet and the combustor of combustion engines to automatically adjust the injection inlet area for optimum performance throughout all engine throttle conditions. The movement of the injection tube cap can increases or decreases the flow of an oxidizer into a combustion chamber. An increase in an operating condition causes the injection tube cap to move in a direction that increases the flow of the oxidizer. A spring mechanism attached to the injection tube cap and the injection tube exerts a force on the cap.

It should be noted that the operating condition could be activated by other than a change in pressure and that materials that expand and contract based on temperature could be substituted for the spring mechanism without deviating from the intent of the invention.

Figure 8:
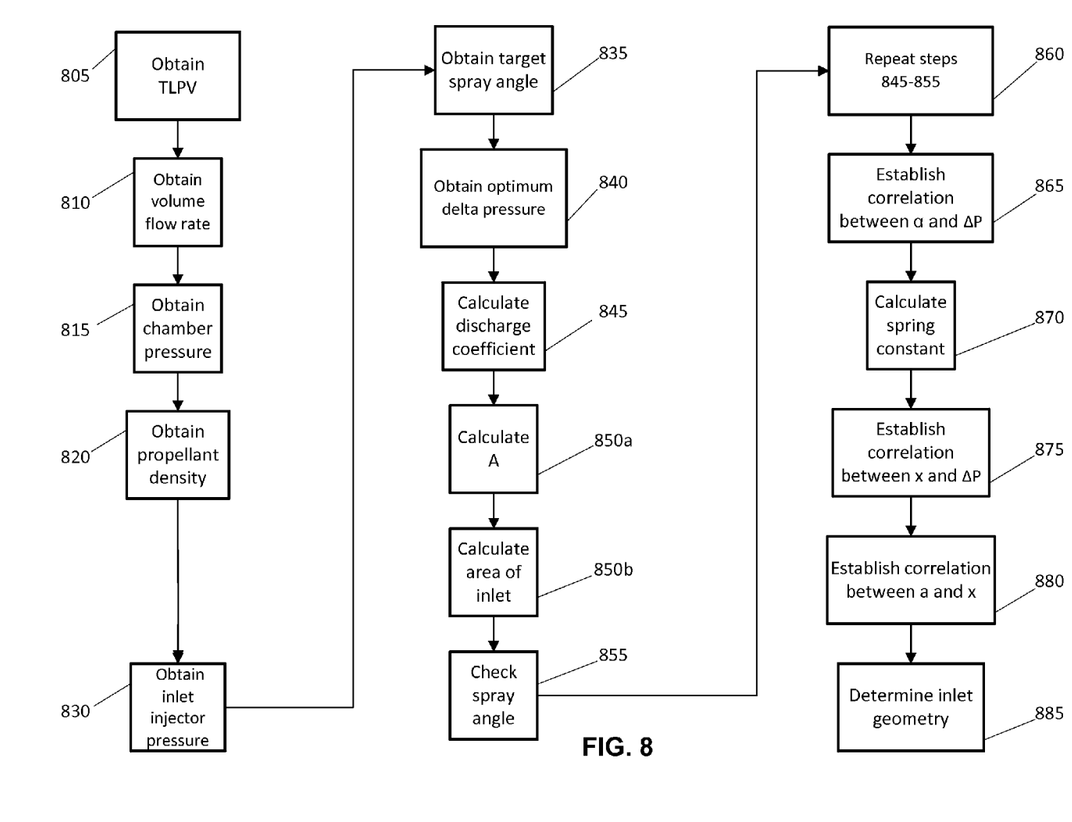
FIG. 8 is a flowchart of a method for determining specific inlet geometries for a given application in accordance with an embodiment.

FIG. 8 is a flowchart depicting an exemplary method 800 for determining specific inlet geometries for a given application. When determining inlet geometries, it is important to keep the value of $\Delta P/P_C$ between 15% and 20%, and the mean spray angle $\theta$ between 60 and 90 degrees. As an engine throttles back, the volume flow rate $\dot{V}$ reduces. Without reducing the value of the discharge coefficient K, the throttling range at which the value of $\Delta P/P_C$ stays between 15% and 20% and the mean spray angle $\theta$ stays between 60 and 90 degrees would be very limited. In order to reduce K, the tangential inlet area would also need to be reduced.

At full throttle, the value of the geometric effectiveness coefficient $d_{eff}$ should be maximized (i.e., $d_{eff}=1$), so at full throttle, inlets should be circular. However, in order to maintain the mean spray angle $\theta$ between 60 and 90 degrees, $d_{eff}$ must decrease when throttling the engine. The value of $d_{eff}$ can be reduced by making the inlets non-circular. At full throttle, the value of $\Delta P/P_C$ is also at a maximum value (i.e., 20%) because this value will drop at lower throttling levels.

Keeping these parameters in mind, method 800 uses known values to calculate inlet geometries.

Method 800 includes obtaining a throttleable level phase value, or TLPV (Step 805). For this specific TLPV, a measured value for the volume flow rate is obtained in Step 810, a measured value for the chamber pressure is obtained (Step 815), a measured value for the density of liquid propellant is obtained (Step 820), a measured value for the inlet injector pressure is obtained (Step 830), a desired or target spray angle is obtained (Step 835) and a desired or target optimum delta pressure value between the inlet and the chamber is obtained (Step 840).

These above values are given based on a specific engine design and requirements. These values do not necessarily need to be obtained in that order, but each of these values is required to calculate the geometric effectiveness coefficient using the $d_{eff}$ to qualitatively determine the shape of the variable inlet aperture.

In Step 845, the discharge coefficient (K) is determined using the equation $$\dot{V}=K\pi r_h^2(2g\Delta P/\rho)^{1/2}$$

where $\dot{V}$ is the fluid volume flow rate, $r_h$ is the radius of the outlet of the injector post, g is the standard gravity constant (32.174 lbm-ft/(lbf-sec$^2$)), $\rho$ is the density of the fluid and $\Delta P$ is the fluid pressure drop across the injector. The standard gravity constant, g, is required for unit conversion when English units are used, but unnecessary when using SI units.

Once the discharge coefficient (K) is determined, a series of equations is used to calculate the inlet area (a). First, in step 850$a$, the following two equations are used to solve for constant A, where both A and $\alpha$ are constants for a given engine situation:

$$K = \frac{\alpha(1-\alpha)^{1/2}}{(1-\alpha+\alpha^2 A^2)^{1/2}}$$

$$A = \frac{1-\alpha}{\left(\frac{\alpha^3}{2}\right)^{1/2}}$$

In step 850$b$, after determining the value of the constant A, the following equation is used to determine the tangential area of the inlet ($\alpha$):

$$A = \frac{\pi r_h R}{a}$$

where R is the radius of the injector post as measured adjacent to the outlet and $r_h$ is the radius of the outlet of the injector.

As illustrated in Step 855, it is possible at this point to use the newly determined tangential area of the inlet ($\alpha$) to check and ensure the mean spray angle $\theta$ is still within the desirable 60 to 90 degree range using the following two equations:

$$A' = \left(\frac{\pi r_h R}{a}\right)\left(\frac{r_h}{R - d_{eff}\sqrt[2]{a/\pi}}\right)$$

$$\theta = 43.5\log 14 A'$$

In Step 855, $d_{eff}$ is an assumed value approximately close to 1, as used for a full throttle condition where inlets are circular. If necessary, however, the value of $d_{eff}$ may be changed by using non-circular inlets, and Step 855 repeated, in order to obtain a $\theta$ within the acceptable range. For example, different engine power levels, or throttling stages, will require smaller $d_{eff}$ in order to maintain $\theta$ between 60 and 90 degrees.

In Step 860, Steps 845 through 855 are repeated for another throttleable level phase value, until the sequence is repeated for each desired throttleable level phase value. The correlation between each calculation of α (tangential area of an inlet) and the ΔP for each throttleable level phase value is established (Step 865).

In Step 870, the spring constant (k) is calculated using the following equation:

$$\Delta P = \frac{kx}{\pi R^2}$$

where x is the displacement of the spring and, because the displacement will be equal, the displacement of the injection tube cap (which adjusts the inlet area). When calculating for k using the above equation, x (displacement) is a known and limited value at the initial and final throttling conditions based on physical limitations. The ΔP for the initial and final throttling conditions is also known.

Because k is now known, the correlation between x (displacement) and ΔP can be established (Step 875).

Using the results of Step 865 and Step 875, the relationship between inlet area (a) and displacement (x) is determined (Step 880), and that relationship used with $d_{eff}$ to determine the injector inlet geometry (Step 885).

What is claimed is:

1. A method for determining the optimum inlet geometry of a liquid rocket engine swirl injector comprised of the steps of:
    obtaining a first throttleable level phase value (TLPV);
    obtaining a first measured value for a volume flow rate;
    obtaining a first measured value for a chamber pressure;
    obtaining a first measured value for a density of liquid propellant;
    obtaining a first measured value for an inlet injector pressure;
    obtaining a first desired target spray angle θ between 60 and 90 degrees;
    obtaining a first desired target optimum delta pressure value between an inlet and a chamber;
    calculating a first tangential inlet area;
    repeating said steps of obtaining a throttleable level phase value, obtaining a measured value for a volume flow rate, obtaining a measured value for a chamber pressure, obtaining a measured value for an inlet injector pressure, obtaining a desired target spray angle θ between 60 and 90 degrees, obtaining a desired target optimum delta pressure value between an inlet and a chamber, and calculating a tangential inlet area;
    establishing a correlation between said calculated tangential inlet areas and said obtained optimum delta pressure values;
    calculating a spring constant;
    determining a spring displacement value for said obtained throttleable level phase values;
    establishing a correlation between said spring displacement values and said obtained optimum delta pressure values;
    establishing a relationship between said tangential inlet areas and said spring displacement values to qualitatively determine the shape of a variable inlet slot;
    wherein the shape of the variable inlet slot has a shape selected from a group of geometric slot shapes consisting of polygon, irregular polygon and oval;
    wherein each of said geometric slot shapes has a geometric shape predetermined geometric effectiveness coefficient value $d_{eff}$;
    wherein $d_{eff}$ is a value equal to or less than 1 and wherein said value is sufficient to maintain the target spray angle θ, wherein θ is calculated as follows:

$$\theta = 43.5 \log 14 \left( \left( \frac{\pi r_h R}{a} \right) \left( \frac{r_h}{R - d_{eff} \sqrt[2]{a/\pi}} \right) \right),$$

wherein $r_h$ is a radius of an outlet of said injector element, R is a radius of said injector element as measured adjacent to said outlet, and a is a tangential area of one of said tangential inlet areas.

2. The method of claim 1 wherein the step of calculating said tangential inlet areas is comprised of the steps of
    calculating a discharge coefficient;
    calculating a constant A; and
    using said constant A to calculate said tangential inlet areas.

3. The method of claim 2 wherein said discharge coefficient is calculated using the equation $\dot{V} = K \pi r_h^2 (2g\Delta P/\rho)^{1/2}$, where K is said discharge coefficient, $\dot{V}$ is said volume flow rate, $r_h$ is the radius of the outlet of an injector element, ΔP is said optimum delta pressure value, ρ is the density of the fluid, and g is the standard gravity constant.

4. The method of claim 2 wherein said constant A is calculated using the equations $$K = \frac{\alpha(1-\alpha)^{1/2}}{(1-\alpha+\alpha^2 A^2)^{1/2}}$$

and $$A = \frac{1-\alpha}{\left(\frac{\alpha^3}{2}\right)^{1/2}},$$

wherein A and α are constants for said throttleable level phase values.

5. The method of claim 1, which further includes the step of adjusting said $d_{eff}$ if said target spray angle is not between 60 and 90 degrees.

6. The method of claim 1 wherein the steps of obtaining a throttleable level phase value, obtaining a measured value for a volume flow rate, obtaining a measured value for a chamber pressure, obtaining a measured value for an inlet injector pressure, obtaining a desired target spray angle between 60 and 90 degrees, obtaining a desired target optimum delta pressure value between an inlet and a chamber, and calculating a tangential inlet area are repeated for a desired range of throttleable level phase values.

* * * * *